United States Patent [19]
Lock et al.

[11] Patent Number: 5,451,235
[45] Date of Patent: Sep. 19, 1995

[54] OCCLUDER AND METHOD FOR REPAIR OF CARDIAC AND VASCULAR DEFECTS

[75] Inventors: James E. Lock, Newton; Rudy Davis, Chelmsford, both of Mass.; George Duval, Lake George, N.Y.

[73] Assignee: C.R. Bard, Inc., Murray Hill, N.J.

[21] Appl. No.: 227,585

[22] Filed: Apr. 14, 1994

Related U.S. Application Data

[63] Continuation of Ser. No. 787,940, Nov. 5, 1991, abandoned.

[51] Int. Cl.$^6$ .............................................. A61B 17/00
[52] U.S. Cl. ................................... 606/213; 606/151; 606/232; 128/899
[58] Field of Search ............... 606/213, 215, 216, 232, 606/220, 151; 623/12; 600/32; 128/898, 899, 887

[56] References Cited

U.S. PATENT DOCUMENTS

| | | | |
|---|---|---|---|
| 3,874,388 | 4/1975 | King et al. | 606/232 |
| 4,007,743 | 2/1977 | Blake | 606/232 |
| 4,041,931 | 8/1977 | Eliott et al. | |
| 4,629,451 | 12/1986 | Winters et al. | |
| 4,710,192 | 12/1987 | Liotta et al. | |
| 4,748,982 | 6/1988 | Horzewski | 604/160 |
| 4,826,487 | 5/1989 | Winter | |
| 4,917,089 | 4/1990 | Sideris | 606/215 |
| 5,052,386 | 10/1991 | Fischer, Jr. | 128/912 X |
| 5,108,420 | 4/1992 | Marks | 606/213 |
| 5,192,301 | 3/1993 | Kamiya et al. | 606/213 |
| 5,254,133 | 10/1993 | Seid | 606/215 |

FOREIGN PATENT DOCUMENTS

| | | | |
|---|---|---|---|
| 581995 | 12/1986 | Australia | |
| 2057018 | 10/1991 | Canada | |
| 2641692 | 7/1990 | France | |
| 57-24132 | 4/1982 | Japan | |
| WO90/14796 | 12/1990 | WIPO | 606/213 |

OTHER PUBLICATIONS

Ruttenberg, Herbert "Nonsurgical Therapy of Cardiac Disorders", *Pediatric Consultant*, vol. 5, No. 2, 1986.

Khan, Ali et al. "Percutaneous Catheter Closure of the Ductus Arteriosus in Children and Young Adults", *American Journal of Cardiology*, Jul. 15, 1989, pp. 218–221.

Lock, James et al. "Transcatheter Closure of Arterial Septal Defects", *Circulation*, vol. 79, No. 5, May 1989, pp. 1091–1099.

Rome, John et al., "Double-Umbrella Closure of Arterial Defects", *Circulation*, vol. 82, No. 3, Sep. 1990, pp.751–758.

Rashkind, William et al. "Congenital Heart Disease, Nonsurgical Closure of Patent Ductus Arteriosus: Clinical Application of the Rashkind PDA Occluder System", *Circulation*, vol. 75, No. 3, Mar. 1987, pp. 583–592.

Bridge et al., *Circulation*, vol. 82, No. 5, Nov. 1990, pp. 1681–1689.

Hellenbrand et al., The Amer. Journal of Cardiology, Jul. 15, 1990, pp. 207–213.

Rome et al., *Circulation*, vol. 82, No. 6, Dec. 1990, pp. 751–758.

Bridge et al., *Circulation*, vol. 86, No. 6, Dec. 1992, pp. 1902–1908.

Primary Examiner—Stephen C. Pellegrino
Assistant Examiner—Jeffrey A. Schmidt
Attorney, Agent, or Firm—Morgan & Finnegan

[57] ABSTRACT

An occlusion device for percutaneous transluminal correction of intracardiac and vascular septal defects is disclosed. The device comprises a pair of opposed occluders that are connected to one another using an interconnection that allows the occluders to move relative to one another. Additionally, a means for fluoroscopically visualizing and distinguishing the individual occluders of the device is also disclosed.

21 Claims, 6 Drawing Sheets

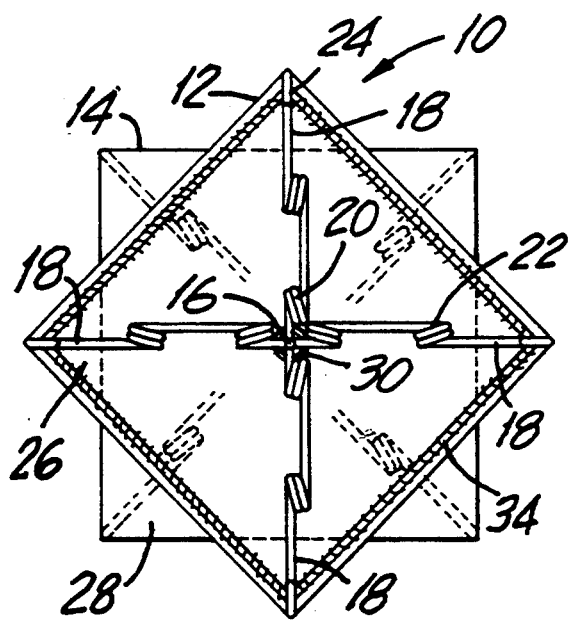
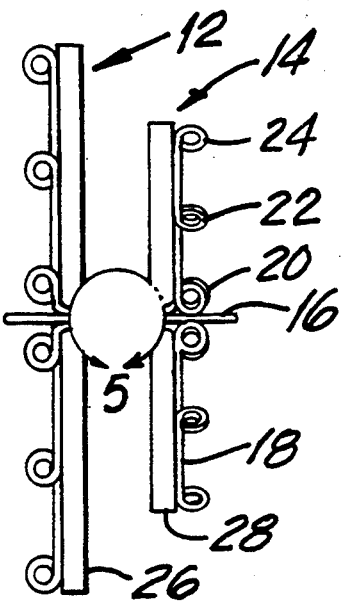
FIG. 1  FIG. 2
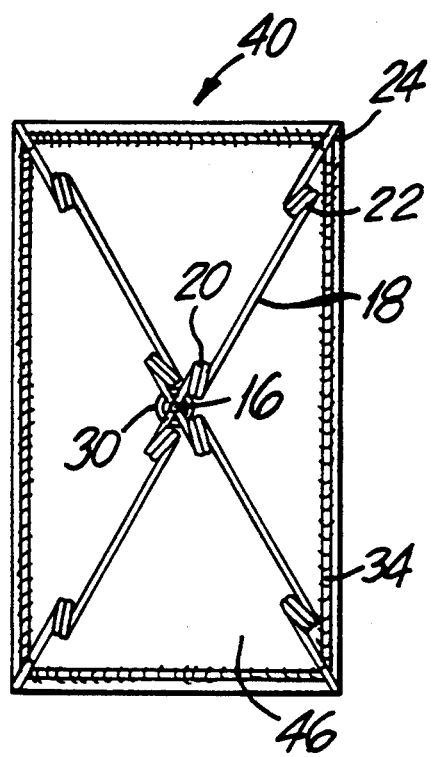
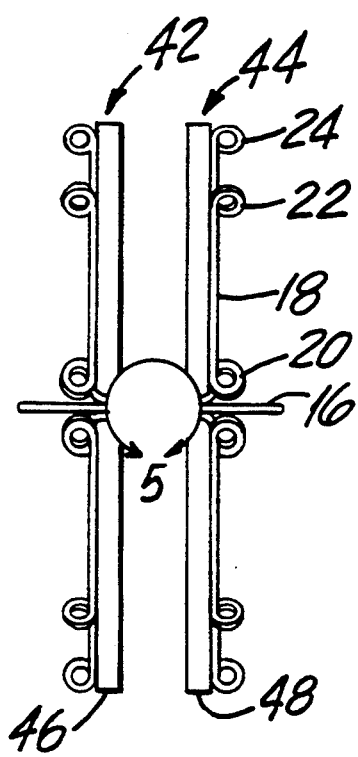
FIG. 3  FIG. 4

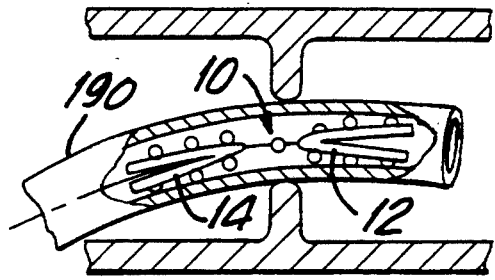
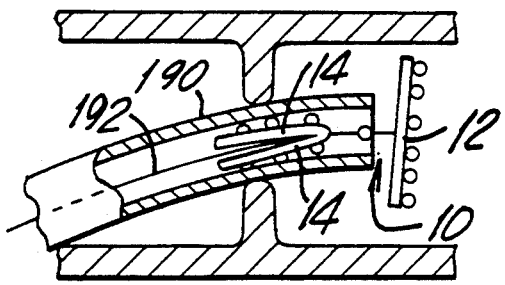
FIG. 8a  FIG. 8b
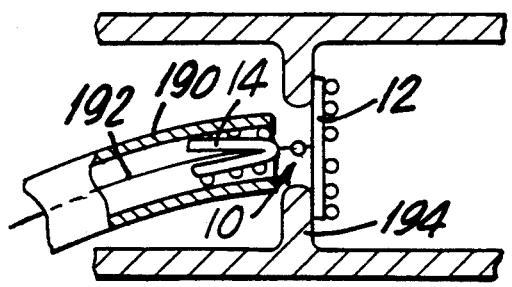
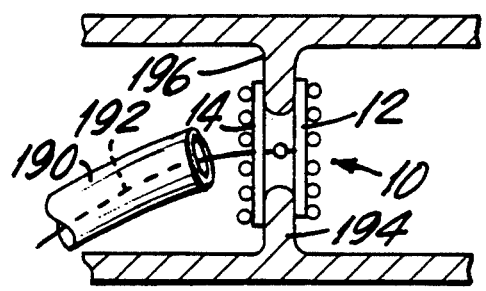
FIG. 8c  FIG. 8d
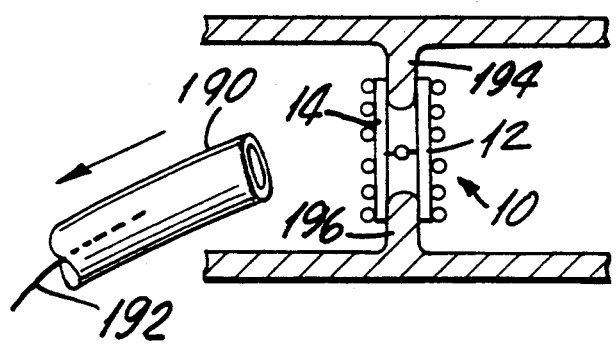
FIG. 8e

OCCLUDER AND METHOD FOR REPAIR OF CARDIAC AND VASCULAR DEFECTS

This is a continuation of application Ser. No. 07/787,940, filed on Nov. 5, 1991 now abandoned.

FIELD OF THE INVENTION

The present invention relates to devices and techniques for the repair of intracardiac and vascular septal defects by percutaneous catheter placement of a corrective prosthetic device.

BACKGROUND OF THE INVENTION

Either congenitally or by acquisition, abnormal openings or holes can occur between adjacent chambers of the heart or its associated major blood vessels. Such openings are referred to, respectively, as interatrial and interventricular septal defects or patent ductus arteriosus and aortico-pulmonary windows. Such openings cause blood to leak from one chamber or artery to another and result in decreased pumping efficiency of the heart. Similarly, if defects occur in the Foramen Ovale, such defects, referred to as Patent Foramen Ovale (PFO), may result in a cerebral embolism. These deformities usually are congenital, however, they can also occur following a heart attack, significantly complicating subsequent coronary treatment and recovery. Such defects typically impose added strain on the heart and ultimately may lead to heart failure if not corrected.

Traditionally, such defects have required extensive open chest surgical techniques for correction. Specifically, the repair of such defects required an open heart procedure in which the heart was exposed and then opened and the defect was sewn shut by direct suturing. In connection therewith, a patch of a synthetic prosthetic material such as Dacron, Teflon, silk, nylon or pericardium was used as a patch.

Although other methods of occluding defects, most notably the use of a plastic plug to occlude the defect, were suggested as early as the 1950s, such methods similarly require the use of open heart surgery to access the defect and place the prosthetic implant.

Beginning in the early 1970s, a number of devices and methods were proposed for the percutaneous transluminal catheterization procedure for the repair of intracardiac defects. For example, U.S. Pat. No. 3,874,388 to King, et al., describes a device in which a pair of umbrella-like occluders are positioned on opposite sides of a defect and drawn and locked together at a central hub which crosses the defect. The device is said to effectively occlude the defect. Although the King device and method proposed to eliminate the need to perform open heart surgery, its use and structure were very complicated in that generally they required the umbrella-like occluders to be opened manually once positioned at the defect.

Similarly, U.S. Pat. No. 4,007,743 to Blake relates to an umbrella-like defect closure device having a plurality of elongated struts pivotally mounted to a central hub. Each pair of adjacent struts is interconnected by a strip formed of a foldable, resilient material which serves to automatically and resiliently open each umbrella-like element once such element is released from a protective sheath. As in the King patent, the device includes two separate occluders which are locked together by a snap connection once each of the occluder segments has been individually positioned across the septal defect.

Still another defect closure device is described in U.S. Pat. No. 4,917,089 to Sideris. The Sideris patent relates to an apparatus and method for transvenous closure of a septal perforation in the heart. The closure apparatus comprises an occluder which is positioned on the distal side of the perforation and an occluder-holder which is positioned on the proximal side of the perforation and is connected to the occluder across the perforation by means of a so-called "button" closure. As in the earlier transluminally delivered occluders, the Sideris patent requires that device elements positioned on opposite sides of a septal defect are separately delivered to the site of the defect and connected to one another in situ.

Among the problems encountered with occluder devices of the designs described by King and Blake, is that they tend to be relatively rigid. In other words, the designs allow very little relative motion between the individual occluder elements and thereby require that each of said elements be placed precisely prior to seating at the septal wall and interconnection. In addition, because the devices described in the King and Blake patents include such relatively rigid structures, the devices are not particularly well suited for applications in which there is a variation in wall thickness at the site of the defect or in which the defect does not run perpendicularly through the septal wall.

Although the Sideris patent describes a device in which the occluder and occluder-holder are not rigidly interconnected, the Sideris device still requires that the occluder be placed precisely on the distal wall portion of the septum because defect occlusion is provided by a single occluder element. Thus, even though there is some amount of relative movement allowed between the occluder and the occluder-holder of the Sideris device, the arms of the occluder are rigid and the occluder section must be precisely positioned to cover the entire distal side of the defect in order to prevent blood from leaking through the defect and to prevent the device from becoming dislodged. Furthermore, like the King and Blake devices, the Sideris device requires in situ assembly to make interconnection between the occluder and the occluder-holder. Such an in situ assembly requirement complicates the occlusion procedure because it requires that the occluder be positioned precisely and then maintained in that position during the assembly step.

Accordingly, there is a need for a defect occlusion device and technique which eliminates the need to assemble or interconnect separate portions of the occluder in situ and which also allows some degree of relative movement or rotation between the individual occluder elements. There is also a need for a defect occlusion device which would allow the individual occluders of the device to be readily distinguished during a fluoroscopic visualization procedure.

SUMMARY AND OBJECTS OF THE INVENTION

The present invention relates to an intracardiac shunt defect occlusion device characterized by having a unitary construction that eliminates the requirement of open chest surgery to place and connect a pair of occlusion devices across a central defect. The device is further characterized in that it includes a means allowing relative movement or rotation between occluder elements (referred to individually as "occluders") positioned on opposite sides of a shunt defect to allow improved seating of the device, particularly when it is to be used in location having uneven walls adjacent to the defect, or in defects that have tunnel-like geometry, such as PFOs or ventricular septal defects located in thicker portions of the septum. In one embodiment, the device comprises proximal and distal occluders each having an umbrella-like configuration. Each occluder has a central hub upon which is mounted a plurality of elongated struts. The struts each include at least one hinge point which allows the struts to be folded parallel to the central axis of the hub, thereby allowing the occluder to be held in a compact, unexpanded configuration. The struts are resilient so that, when released, they automatically expand to an orientation perpendicular to the central axis of the occluder.

An interconnection means is provided at each of the central hubs to connect the occluders to one another. The interconnection means allows relative movement between the occluders so that they can be positioned across a defect which has a nonuniform wall thickness or which has openings which are offset across the septal wall. The interconnection means can be of any of a variety of configurations, however, interconnecting loops and ball and collar assemblies are preferred.

At least one strut of at least one of the occluders is at least partly radiopaque to allow fluoroscopic visualization of the occluder during the catheter placement procedure. Additionally fluoroscopic visualization is useful after the procedure has been completed in order to monitor the location and orientation of the occluder post-operatively. Such radiopacity can be provided either by forming the strut of a radiopaque material (either metallic or non-metallic), or by providing a radiopaque material upon a surface of a non-radiopaque strut. Among the preferred radiopaque materials are gold and platinum. In addition, each of the occluders may be provided with a radiopaque material that allows the individual occluder elements to be distinguished from one another during fluoroscopic visualization. This further enhances the ability of a physician to determine the precise location, position and orientation of the occluder device during and after the placement procedure.

Thus, it is one object of the present invention to provide a septal defect occlusion device that eliminates the need to assemble or interconnect individual occluder elements in situ.

It is another object of the present invention to provide a septal defect occlusion device having individual occluders which are connected to one another prior to insertion into a patient.

It is a further object of the invention to provide a septal defect occlusion device which allows relative motion of individual occluder elements to one another during percutaneous catheter placement of the occlusion device within a patient.

It is yet another object of the present invention to provide a septal defect occlusion device which can be placed across defects present in septal walls having a nonuniform thickness, such as the tunnel-like defects described previously.

It is still another object of the present invention to provide a septal occlusion device for occluding a septal defect having offset openings on opposite sides of the septal wall.

It is a further object of the present invention to provide a septal defect occlusion device that can be readily visualized in vivo using fluoroscopic means.

It is yet another object of the present invention to provide a septal defect occlusion device that allows the location, position and orientation of the individual occluders to be visualized and distinguished using fluoroscopic means.

It is still another object of the present invention to provide a method for positioning an occlusion device across a defect.

Other objects and features of the present invention will become apparent from the following detailed description when taken in connection with the accompanying drawings which disclose multiple embodiments of the invention. It is to be understood that the drawings are designed for the purpose of illustration only, and are not intended as a definition of the limits of the invention.

BRIEF DESCRIPTION OF THE DRAWINGS

FIG. 1 is a representation of one occlusion device of the present invention.

FIG. 2 is a side view of the device shown in FIG. 1.

FIG. 3 is a schematic representation of a second embodiment of an occlusion device of the present invention.

FIG. 4 is a side view of the device depicted in FIG. 3.

FIGS. 8a–8e depict a method of placing an occlusion device across a septal defect.

DETAILED DESCRIPTION OF THE PREFERRED EMBODIMENTS

Figure 5B:
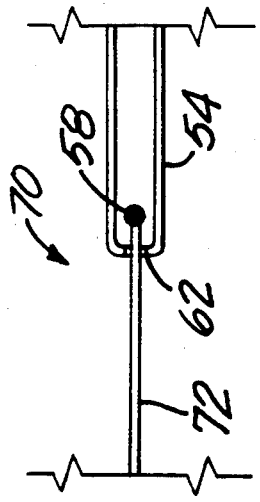
FIGS. 5a–5k are schematic representations of various interconnection structures for connecting the elements of the occlusion devices depicted in FIGS. 1–4.

In one embodiment of the present invention, the device 10 comprises a first occluder 12 connected to a second occluder 14 (shown largely in phantom in FIG. 1) in a face-to-face relationship. The occluders 12, 14 are connected to each other by means of a central hub or wire 16 which defines a central axis through each of the occluders 12, 14. It is noted that as used herein, the term "central axis" is not meant to imply that the wire or hub necessarily is positioned at the geometric center, if any, of its respective occluder. Rather, the term is intended to describe a reference line oriented in a perpendicular relationship to the plane of each occluder, the line passing through any given reference point on the occluder.

Each occluder comprises generally a plurality of elongated struts 18 which radiate from the central hub 16 and provide a framework for the occluder. The framework can be collapsed and then automatically opened by resilient means which are provided in each of the elongated struts 18. Specifically, each strut includes at least one flexural hinge point or shoulder 20 about which the elongated strut 18 may flex. In a collapsed configuration, the elongated struts 18 are pivotally flexed about the hinge points 20 to cause the struts to be oriented in a position that is generally parallel to the central axis of the occluder defined by the hub or wire 16. The struts are maintained in this position against resilient forces by enclosing the device within a tubular sheath at the distal end of a delivery catheter which maintains the device in a collapsed configuration. Upon withdrawal of the sheath during the placement procedure, resilient forces stored within the elongated struts at flexural hinge points 20 cause the device to spring open by pivoting the struts about the hinge points 20. The struts 18 open to an orientation generally perpendicular to the central axis defined by the hub 16 of the occluder.

A second flexural hinge point or elbow 22 can be provided on the struts 18 to further enhance operation of the device. The second flexural hinge provides a point about which the strut arm itself can fold, thereby allowing the length of the strut in its folded configuration to be shortened. Each strut preferably also includes a loop 24 at its outer end to conceal sharp areas that might otherwise cause damage to a patient's tissue during insertion and placement of the device 10.

The material which comprises the strut structures can be any biocompatible material having resilient and structural properties sufficient for operation of the device. In particular, stainless steel wire is preferred for fabrication of the strut structures.

Attached to the strut frameworks are patches 26, 28 which, when the device is deployed, cover and occlude the shunt defect. Although numerous biocompatible materials can be used as the patch material, preferred patch materials comprise Dacron, Teflon, silk, nylon or pericardium tissue. Among the necessary characteristics of the patch material are bicompatibility and resistance to fluid transfer across the material. The material must be such that these properties can be maintained for extended periods in vivo. Additionally, the patch material must be flexible to allow the occluder device to be folded and compressed within a sheath prior to and during delivery to a predetermined location within a patient. An aperture 30 is formed within the center of each of the patches 26, 28 and allows an interconnecting structure (described in connection with FIGS. 5a–5k) to connect the occluder elements 12, 14 to each other.

The patches 26, 28 are held to the strut framework by a plurality of stitches formed from sutures which encircle the struts and pass through the patch material. In a preferred embodiment, the stitches attach the patches to the framework at least at the regions at which the pivot points 20, 22 and loops 24 contact the patch material. Alternatively, the sutures can be tied off at each loop 24 and spiraled through the patch material and toward the central hub 16, terminating with knots tied to the pivot points 20.

A ribbing 34 formed by a series of closely placed stitches is preferably formed along the peripheral edges of the patch material. The ribbing 34 provides an area of increased patch material thickness and serves to provide a degree of stiffness and support to the outer edge of the patch material.

In the illustrative embodiment depicted in FIGS. 1 and 2, each of the occluders 12, 14 is square. To more clearly depict the relationship between the occluders in FIG. 1, occluder 14 has been rotated 45° to provide an offset in the face-to-face relationship.

FIGS. 3 and 4 are similar to FIGS. 1 and 2 with the exception that the occlusion device 40 of FIGS. 3 and 4 comprises occluders 42, 44 that are rectangular in shape rather than being square as depicted in FIGS. 1 and 2. Specifically, the device depicted in FIGS. 3 and 4 includes a framework made of elongated struts 18 having flexural hinge points 20, 22 which allow the struts to be maintained in a compressed state in a direction generally parallel to a central axis defined by a wire or hub 16 of each occluder element 42, 44. As in FIGS. 1 and 2, each of the elongated struts 18 includes a loop 24 at its outermost end to reduce the risk of trauma in vivo. In addition, the strut structure of each occluder 42, 44 includes a ribbing 34 formed of closely spaced sutures to provide a degree of stiffness and support to the outer edge of the patch material 46, 48. As before, the patches 46, 48 can be fabricated of biocompatible materials with materials such as Dacron, Teflon, silk, nylon or pericardium being preferred. The patches 46, 48 are attached to the strut framework using suture thread as described previously. Additionally, each of the rectangular occluder elements 42, 44 includes an aperture 30 through which interconnection between the individual occluder elements 42, 44 can be made.

Although depicted as having a square or rectangular geometry in FIGS. 1–4, it is pointed out that the shape of the occluder elements is not intended to be limited as such. Rather, occluders having circular or other geometries are contemplated as well, and are intended to be encompassed within the scope of the invention.

Figure 5A:
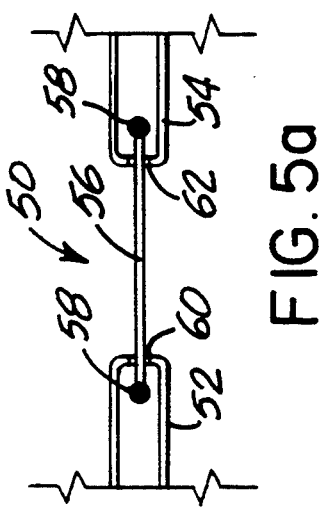

FIGS. 5a–5k depict the various structures for interconnecting the occluder elements of the devices of FIGS. 1–4 in a manner that allows relative pivotal (and, in some cases, rotational) movement between the individual occluder elements and/or rotation thereof. Specifically, FIG. 5a depicts an interconnection 50 in which individual collar elements 52, 54 are connected by a pin 56 having ball fittings 58 attached to the ends thereof. The ball fitting 58 are designed to be larger in diameter than apertures 60, 62 contained within the collar members 52, 54 thereby allowing the collars to move toward or away from each other while preventing the pin 56 from being released therefrom. The interconnection also provides for collar members 52, 54 having central axes that are not parallel to each other or to the pin 56. The collar members 52, 54 are also free to rotate relative to each other. In such an assembly, each of the collar members 52, 54 is connected to the strut framework of one of the occluder elements 12, 14 or 42, 44 respectively, through the aperture 30 to allow the collar element to constitute an integral structure to the strut framework of the occluder element. Similar to the strut framework of the occluder element, the components of the interconnection 50 can comprise a biocompatible material with a material such as stainless steel being preferred. The interconnection 50 depicted in FIG. 5a is characterized in that it provides, in essence, two regions about which relative movement of the occluder element attached to the collar members can occur.

FIG. 5b depicts an interconnection 70 similar to the interconnection 50 of the device shown in FIG. 5a. Unlike interconnection 50, however, the interconnection 70 provides only one region of relative movement between the occluder elements 12, 14 or 42, 44 which it interconnects. Specifically, the interconnection 70 includes a collar element 54 having an aperture 62 therein. A pin 72 with a ball member 58 having a diameter greater than that of the aperture 62 serves to lock pin 72 to the collar element 54. The pin 72 is connected to one strut framework of an occluder element while the collar 54 is connected to the strut framework of an opposing occluder element thereby serving to interlock the two occluder elements to each other in a face-to-face arrangement.

Figure 5G:
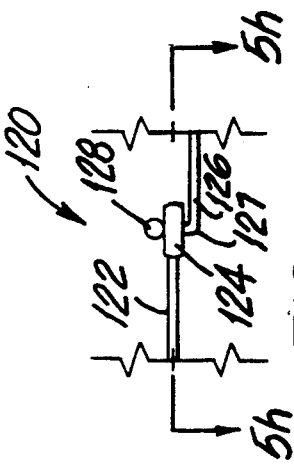
Figure 5I:
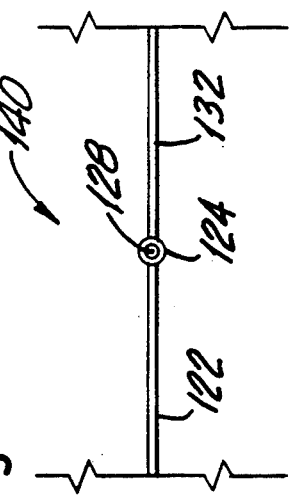
Figure 5H:
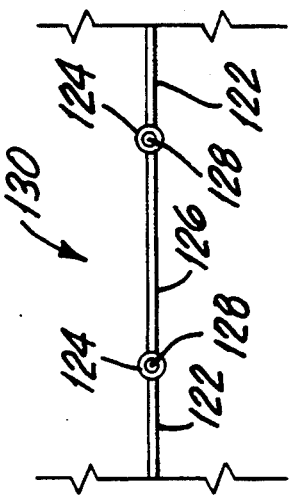
Figure 5C:
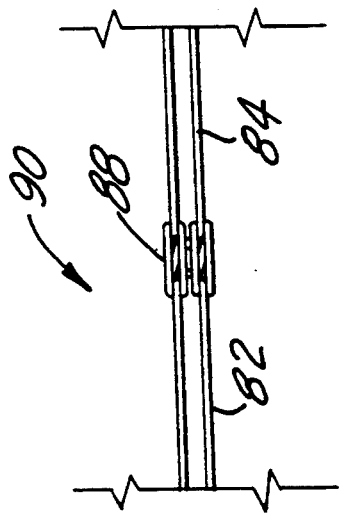

FIG. 5c depicts another embodiment of an interconnection 80 in which loops 82, 84 connected to the strut frameworks of individual occluder elements 12, 14 or 42, 44 are interconnected by means of a central link 86. The central link is connected to each of the loops 82, 84 via connection coils 88. As shown in FIG. 5c, each connection coil 88 comprises four loops which serve to connect loops 82, 84 to opposite ends of link 86. Like interconnections 50 and 70, interconnection 80 provides an interconnection structure having two regions of movement; however, unlike those interconnection means, the interconnection 80 does not allow substantial relative rotation between occluder elements that are connected therewith.

Figure 5D:
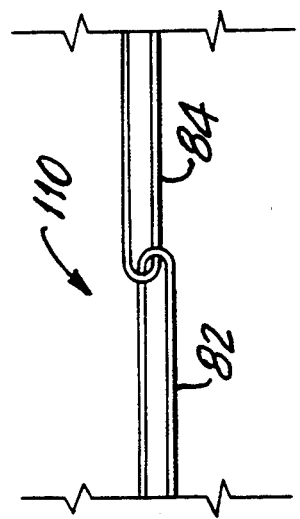

FIG. 5d depicts a similar interconnection 90 having only one region of movement. In FIG. 5d the interconnection includes a first loop 82 connected to one strut framework and a second loop 84 connected to the strut framework of an opposing occluder element. Loops 82 and 84 are linked by a connecting coil 88 in the same manner as depicted in FIG. 5c. Like the interconnection 80 depicted in FIG. 5c, interconnection 90 allows relative movement between occluder elements connected to loops 82, 84 without allowing substantial relative rotational movement therebetween. As in the previous embodiments, interconnections 80 and 90 of FIGS. 5c and 5d are formed of a biocompatible material, with stainless steel being preferred.

Figure 5E:
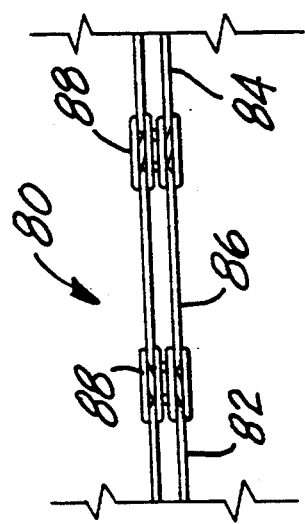

Still another embodiment of an interconnection 100 is depicted in FIG. 5e. In FIG. 5e, loops 82, 84 connected to individual occluder elements 12, 14 or 42, 44 are connected by means of an interconnecting link 86 to form, generally, a three link chain for interconnecting the individual occluder elements. The design of the interconnection 100 shown in FIG. 5e can be considered to be a hybrid of the interconnection means depicted previously. Specifically, interconnection 100 provides two regions of movement between the connected occluder elements and also allows some limited rotation between such elements. Thus, although not allowing complete rotation as allowed by interconnections 50 and 70, the interconnection 100 will allow greater rotational movement than can be achieved by interconnections 80, 90.

Figure 5F:
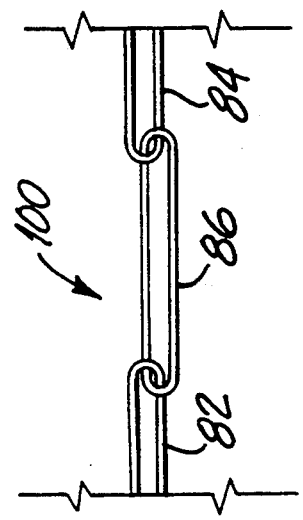

FIG. 5f depicts a similar interconnection 110 in which the central link 86 has been eliminated and loops 82, 84 are directly linked to one another. This connection can be viewed generally as a two link chain with each link 82, 84 being connected to an individual occluder element 12, 14 or 42, 44. Such an interconnection 110 offers one region of relative movement between the occluder members 12, 14 and also allows some rotational motion between such occluder elements, however, such rotation is limited. As before, the interconnections 100, 110 depicted in FIGS. 5e and 5f are formed of a biocompatible material, preferably stainless steel.

FIGS. 5g–5i depict yet another embodiment of an interconnection in which a ball and collar is used to provide a pivoting connection point. The ball and collar interconnection 120 is depicted in elevation in FIG. 5g. Specifically a connecting rod 122 includes circular collar 124 or loop at one end. A pin 126 having a bend 127 of approximately 90° at one end has a ball 128 mounted on the end adjacent to the bend 127. The diameter of the ball 128 is greater than the inner diameter of the collar 124 to thereby cause a pivoting interference connection between the connecting rod 122 and the pin 126.

FIG. 5h depicts a top view of an interconnection 130 having two pivoting ball and collar joints. Each of the connecting rods 122 are connected to opposing occluder elements, and each have a collar 124 at the end opposite the occluder element. A pin 126 having balls 128 at each end thereof is positioned between the connecting rods in a manner to provide a pair of pivoting connections as set forth in FIG. 5g above.

FIG. 5i depicts a similar interconnection 140 having only one pivot point. In FIG. 5i, a first connecting rod 122 and collar 124 is connected with a second connecting rod 132 having a ball 128 at one end. Unlike the interconnection of FIG. 5h, the interconnection of FIG. 5i has replaced the pin with a second connecting rod 132 that connects directly to an occluder element.

Figure 5J:
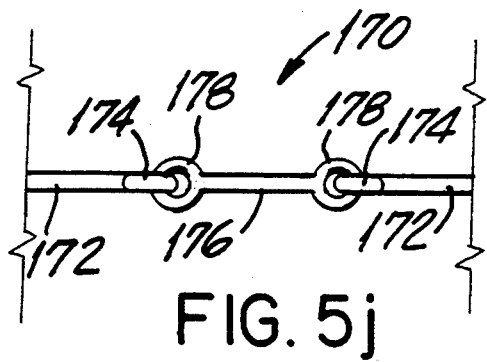

FIG. 5j depicts an interconnection 170 having two pivoting loop joints. Each of the connecting rods 172 are connected to opposing occluder elements, and each have a loop 174 at the end opposite the occluder element. A pin 176 having loops 178 at each end thereof is positioned between the connecting rods. The loops 178 on the pin 176 are linked with the loops 174 on the connecting rods 172 in a chain-like manner to provide a pair of pivoting connections between each of the connecting rods and their respective occluders.

Figure 5K:
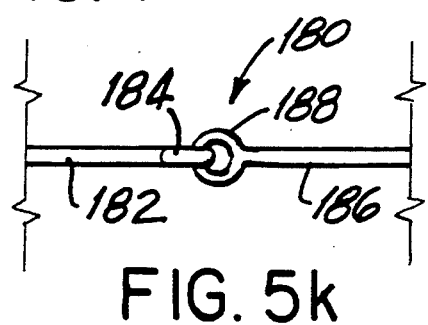

FIG. 5k depicts a similar interconnection 180 having only one loop joint. In FIG. 5k, a first connecting rod 182 having a loop 184 is connected with a second connecting rod 186 having a loop 188 at one end. The interconnection is acheived by interlocking the loops 184 and 188 in a chain-like manner to provide a pivoting loop connection. Unlike the interconnection of FIG. 5j, the interconnection of FIG. 5k has replaced the pin with a second connecting rod 186 that connects directly to an occluder element.

Although the invention is not intended to be limited to any specific dimensions, it is noted that the length of the connector can be selected to correspond to the length of the defect across which the occluder elements are connected. Connectors having lengths of 0.100 inches, 0.200 inches and 0.300 inches are particularly preferred.

Figure 6:
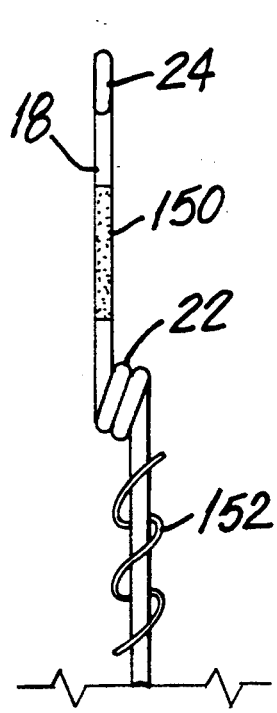
FIG. 6 is a schematic representation of a portion of an occluder having radiopaque portions.
Figure 7:
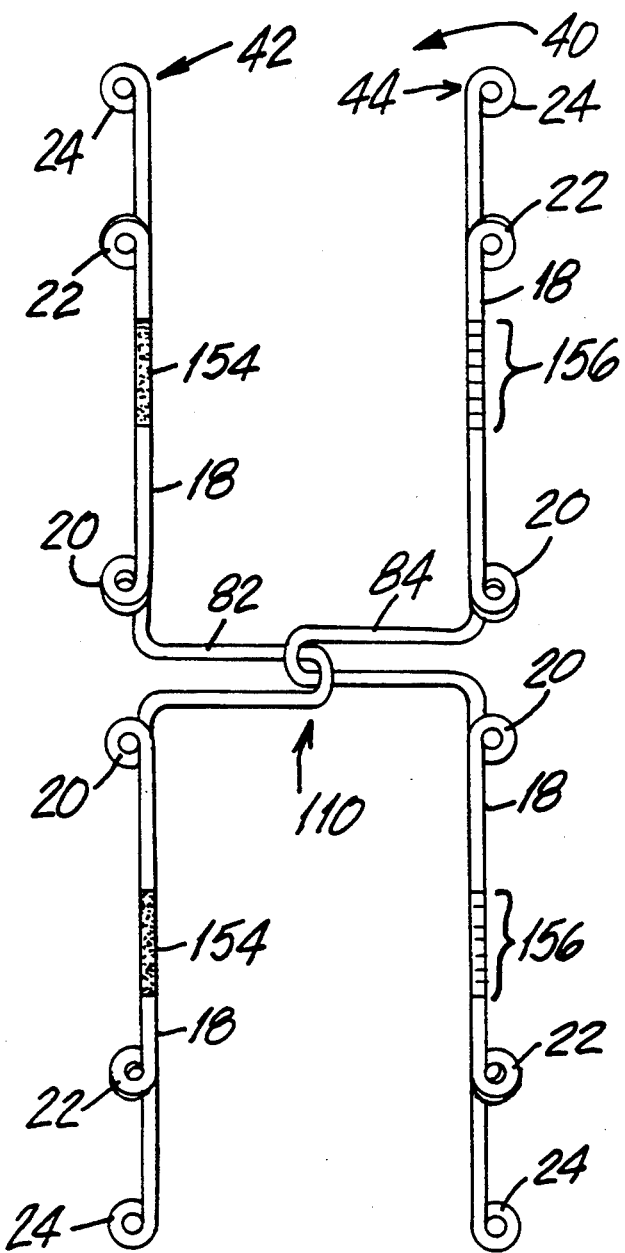
FIG. 7 is a schematic representation of an occlusion device having fluoroscopically distinguishable occluders.

As depicted in FIG. 6, it is preferred that at least one strut 18 of each occluder be provided with a radiopaque material 150 to allow fluoroscopic visualization thereof. Such a material can comprise a coating of gold around one or more of the struts of each occluder element or, alternatively, can include a segment of platinum wire 152 wrapped about a portion of such strut. Additionally, as shown in FIG. 7, (in which only the strut framework is shown for purposes of clarity), interconnected occluders 42, 44 can have respective radiopaque portions 154, 156 that are distinguishable, thereby allowing the individual occluders 42, 44 to be readily distinguished by fluoroscopic visualization techniques during a surgical procedure. Thus, the occlusion device 40 of FIGS. 3, 4 and 7 could include an occluder 42 having a continuous radiopaque material 154 applied to its struts 18 and an occluder 44 with a striped radiopaque material 156 applied to its struts. As such, during fluoroscopic visualization, a physician would be able to determine the relative position of each occluder by determining whether the struts that were being observed had a continuous or a striped radiopaque coating.

Alternatively, one occluder could have two adjacent struts with a radiopaque coating whereas the second occluder could have two opposite struts having the coating of radiopaque material. As before, such a difference would allow the physician to readily distinguish the different occluders from one another and determine the relative positions of the occluders using fluoroscopic visualization techniques. In yet another embodiment, the location of the radiopaque material can be varied between the two occluders to allow each occluder to be readily distinguished. For example, one occluder could include radiopaque material located on the struts directly adjacent to the hub portion of the strut framework whereas the opposing occluder could include radiopaque material deposited on the outer end of the struts forming the strut framework. Such a configuration would allow the individual occluders to be readily distinguished during fluoroscopic visualization of the device during a surgical implantation.

In one protocol for use, the struts of each occluder are folded back against resilient forces to orient the struts generally parallel to the central axis of each occluder. Such a configuration causes the patch material to take on a fan- or umbrella-fold configuration between the folded struts. By forcing each strut into an orientation generally parallel to the central axis of the device, the device is provided with a smaller, unexpanded configuration that allows the device to be percutaneously transluminally inserted into a patient while contained within a tubular sheath at the end of a catheter 190 and guided to a predetermined location. Specifically, as shown in FIG. 8a the compressed device 10 is inserted into a catheter 190 with one occluder 12 positioned distally to the second, connected occluder 14. The catheter 190, with the compressed occlusion device 10 contained in a distal portion thereof is inserted into a blood vessel of a patient and is navigated through the patient's blood vessels into the heart and across the septal defect. At that point, as shown in FIG. 8b the occlusion device is moved distally relative to the sheath to cause the distal occluder 12 to exit the distal end of the catheter 190. Such relative movement can be accomplished either by advancing the occlusion device within the catheter by means of a positioning wire 192 or by retracting the catheter while holding the occlusion device in place with the positioning wire. Once the distal occluder has been advanced beyond the distal end of the catheter sheath 190, the occluder 12 will automatically and resiliently open to its expanded configuration with the strut framework extending perpendicularly to the central axis of the element.

As shown in FIG. 8c the catheter and occlusion device then are gently retracted to seat the distal occluder element 12 against the distal wall surface 194 of the septum in a manner such that a defect though the septum is occluded. As shown in FIG. 8d, the catheter sheath 190 then is further withdrawn a sufficient distance to allow the proximal occluder 14 to be released from the distal end of the catheter sheath. Once released, the proximal occluder 14 opens automatically and resiliently in the same manner as the distal occluder 12. Upon opening, the proximal occluder lies against the proximal surface 196 of the septal wall in an area of a septal defect thereby occluding such defect from the proximal side. The catheter sheath and positioning wire are then withdrawn from the patient leaving the opened occlusion device 10 with occluder elements 12, 14 positioned on each side of a septal defect and permanently implanted within the patient as shown in FIG. 8e.

Figure 9:
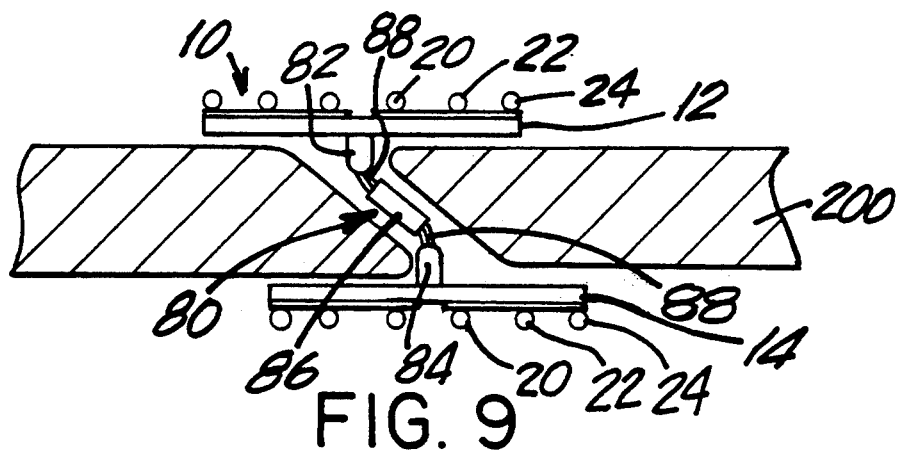
FIG. 9 is a schematic representation of an occlusion device placed across an angled defect.
Figure 10:
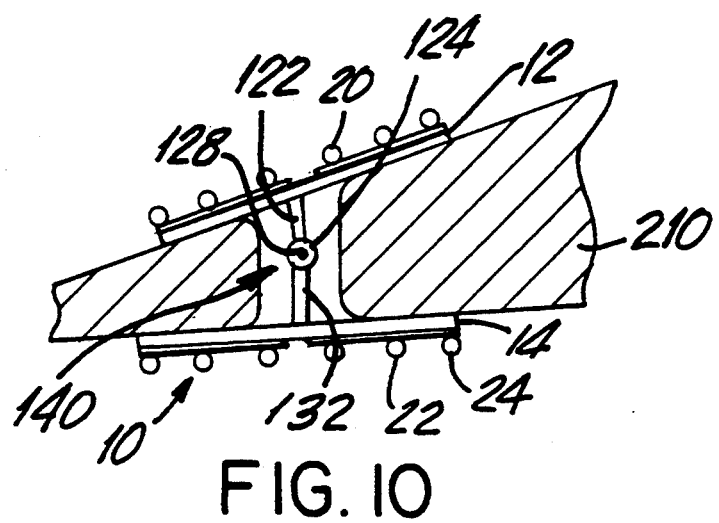
FIG. 10 is a schematic representation of an occlusion device placed across a defect in tissue having a nonuniform wall thickness.

Because the occluder elements are free to move relative to each other, (and in some embodiments to rotate as well), the occlusion device can be used in applications in which it is desirable that the occluder elements are not directly opposed to one another. For example, such an occluder device can be used to correct flap-like or tunnel-like defects in the atrial septum. As shown in FIG. 9 such a device also is useful particularly for the occlusion of defects in which the defect is an angled defect through the septal wall rather than perpendicular. In FIG. 9, the occlusion device 10 having a connection 80 is used to repair an angled defect in the heart wall 200. Similarly, as shown in FIG. 10, the device also is useful for defects that occur at septal locations that do not have a uniform wall thickness. In FIG. 10, the occlusion device 10 having a connection 140 is used to repair a defect in a tissue portion 210 having a non-uniform wall thickness.

Equivalents

Although the specific features of the invention are shown in some drawings and not in others, this is for convenience only, as each feature may be combined with any or all of the other features in accordance with the invention.

Thus, the invention provides an occlusion device which allows relative pivotal and/or rotational movement between occluders positioned on opposite sides of the defect. In addition the invention provides an occlusion device which allows the individual occluders to be distinguished using fluoroscopic visualization.

It should be understood, however, that the forgoing description of the invention is intended merely to be illustrative thereof, that the illustrative embodiments are presented by way of example only and that other modifications, embodiments, and equivalents may be apparent to those skilled in the art without departing from its spirit.

Having thus described the invention, what we desire to claim and secure by Letters Patent is:

1. A device for percutaneous transluminal repair of septal defects comprising:
  a) a first occluder having an initial cross sectional configuration smaller than that of the defect to be repaired and a second expanded configuration larger than that of the detect;
  b) a second occluder having an initial cross sectional configuration smaller than that of the detect to be repaired and a second expanded configuration larger than that of the defect; and
  c) said first occluder and said second occluder being connected by a connector means for fastening the first occluder to the second occluder said connector means comprising a pivot means for allowing rotation of the first occluder relative to the second occluder when said occluders are in the expanded configuration.

2. The device of claim 1 wherein at least one of said first occluder or said second occluder comprises a central hub having a plurality of elongated struts radiating therefrom.

3. The device of claim 2 wherein at least one of said elongated struts comprises a radiopaque material.

4. The device of claim 2 wherein at least one of said elongated struts includes a radiopaque material on at least one surface thereof.

5. The device of claim 4 wherein each occluder includes at least one elongated strut having a radiopaque material on at least one surface thereof.

6. The device of claim 5 wherein the radiopaque material on the first occluder provides a visualization that is distinct from the radiopaque material on the second occluder.

7. The device of claim 2 wherein at least one of said elongated struts includes a flexural hinge point located adjacent to the central hub.

8. The device of claim 7 wherein said at least one elongated strut includes a flexural hinge point at a location remote from the central hub.

9. The device of claim 2 wherein at least one of said elongated struts includes a flexural hinge point at a location remote from the central hub.

10. The device of claim 2 wherein at least one of said elongated struts includes a loop at a distal end thereof away from the central hub.

11. A device for percutaneous transluminal repair of septal defects comprising:
   a) first occluder having an initial cross sectional configuration smaller than that of the defect to be repaired and a second expanded configuration larger than that of the defect;
   b) a second occluder having an initial cross sectional configuration smaller than that of the defect to be repaired and a second expanded configuration larger than that of the defect; and
   c) said first occluder and said second occluder being connected by a connector means for fastening the first occluder to the second occluder said connector means comprising a linked loop assembly for allowing relative movement between the first occluder and the second occluder when said occluders are in the expanded configuration, wherein a loop connected to the first occluder is linked to a loop connected to the second occluder.

12. A device for percutaneous transluminal repair of septal defects comprising:
   a) a first occluder having an initial cross sectional configuration smaller than that of the defect to be repaired and a second expanded configuration larger than that of the defect;
   b) a second occluder having an initial cross sectional configuration smaller than that of the defect to be repaired and a second expanded configuration larger than that of the defect; and
   c) said first occluder and said second occluder being connected by a connector means for fastening the first occluder to the second occluder said connector means comprising a ball and collar assembly for allowing relative movement between the first occluder and the second occluder when said occluders are in the expanded configuration, said assembly comprising a collar connected to one of the first and second occluders with an aperture and a pin with a ball fitting connected to the other of the first and second occluders on at least one end thereof wherein a diameter of said ball fitting is larger than a diameter of the aperture in the collar.

13. A method for percutaneous transluminal repair of septal defects in a patient comprising the steps of:
   a) providing an occlusion device comprising a first occluder having an initial cross sectional configuration smaller than that of the defect to be repaired and a second expanded configuration larger than that of the defect, a second occluder having an initial cross sectional configuration smaller than that of the defect to be repaired and a second expanded configuration larger than that of the defect, and a connector means for connecting the first occluder to the second occluder the connector means comprising a linked loop assembly which allows relative movement between the first occluder and the second occluder when said occluders are in the expanded configuration, wherein a loop connected to the first occluder is linked to a loop connected to the second occluder;
   b) inserting the occlusion device with the first and second occluders in their initial configurations into a distal portion of a catheter sheath;
   c) transluminally guiding the distal portion of the catheter sheath to a first position on a first side of the defect;
   d) advancing the occlusion device relative to the sheath to release the first occluder and allow it to expand to its second configuration on said first side of the defect;
   e) moving said distal portion of the catheter sheath to a second position on a second side of the detect;
   f) retracting the catheter sheath to thereby release the second occluder and allow it to expand to its second configuration on said second side of the defect; and
   g) withdrawing the sheath while leaving the occlusion device in position across the defect.

14. The method of claim 13 wherein at least one of said occluders is fluoroscopically visible.

15. The method of claim 14 wherein both of the occluders are fluoroscopically visible.

16. The method of claim 15 wherein the first occluder can be distinguished from the second occluder.

17. The method of claim 13 comprising guiding the distal portion of the catheter sheath to a first position on a first side of a tunnel-like defect.

18. The method of claim 13 comprising guiding the distal portion of the catheter sheath to a first position on a first side of a defect which is present in a region of a septum having a non-uniform wall thickness.

19. A method for percutaneous transluminal repair of septal defects in a patient comprising the steps of:
   a) providing an occlusion device comprising a first occluder having an initial cross sectional configuration smaller than that of the defect to be repaired and a second expanded configuration larger than that of the defect; the first occluder fastened to a second occluder having an initial cross sectional configuration smaller than that of the defect to be repaired and a second expanded configuration larger than that of the defect, the first occluder fastened to the second occluder by a linked loop assembly in which a loop connected to the first occluder is linked to a loop connected to the second occluder, wherein at least one of the first occluder or the second occluder includes a radiopaque gold coating on at least one surface thereof that allows such occluder to be fluoroscopically distinguished from the other occluder;
   b) inserting the occlusion device with the first and second occluders in their initial configurations into a distal portion of a catheter sheath;
   c) transluminally guiding the distal portion of the catheter sheath to a first position on a first side of the defect;

d) advancing the occlusion device relative to the sheath to release the first occluder and allow it to expand to its second configuration on said first side of the defect;
e) moving said distal portion of the catheter sheath to a second position on a second side of the defect;
f) retracting the catheter sheath to thereby release the second occluder and allow it to expand to its second configuration on said second side of the defect; and
g) withdrawing the sheath while leaving the occlusion device in position across the defect.

20. The method of claim 19 comprising guiding the distal portion of the catheter sheath to a first position on a first side of a tunnel-like defect.

21. The method of claim 19 comprising guiding the distal portion of the catheter sheath to a first position on a first side of a defect which is present in a region of a septum having a non-uniform wall thickness.

* * * * *